United States Patent
Sheldon et al.

(10) Patent No.: US 9,446,248 B2
(45) Date of Patent: Sep. 20, 2016

(54) INTERVENTIONAL MEDICAL SYSTEMS, TOOLS, AND METHODS OF USE

(71) Applicant: Medtronic, Inc., Minneapolis, MN (US)

(72) Inventors: Todd J Sheldon, North Oaks, MN (US); Matthew D Bonner, Plymouth, MN (US); Kathryn Hilpisch, Cottage Grove, MN (US); Noelle C Neafus, Lino Lakes, MN (US); Ronan Wood, Co. na Gaillimhe (IE)

(73) Assignee: Medtronic, Inc., Minneapolis, MN (US)

( * ) Notice: Subject to any disclaimer, the term of this patent is extended or adjusted under 35 U.S.C. 154(b) by 148 days.

(21) Appl. No.: 14/518,128

(22) Filed: Oct. 20, 2014

(65) Prior Publication Data

US 2016/0015983 A1  Jan. 21, 2016

Related U.S. Application Data

(60) Provisional application No. 62/025,620, filed on Jul. 17, 2014, provisional application No. 62/041,927, filed on Aug. 26, 2014.

(51) Int. Cl.
| | |
|---|---|
| *A61B 19/00* | (2006.01) |
| *A61N 1/37* | (2006.01) |
| *A61B 17/34* | (2006.01) |
| *A61M 25/00* | (2006.01) |
| *A61N 1/372* | (2006.01) |

(Continued)

(52) U.S. Cl.
CPC ........... *A61N 1/371* (2013.01); *A61B 17/3468* (2013.01); *A61M 25/0082* (2013.01); *A61N 1/372* (2013.01); *A61B 2018/00642* (2013.01); *A61N 1/056* (2013.01); *A61N 1/0573* (2013.01); *A61N 1/3756* (2013.01); *A61N 1/37205* (2013.01); *A61N 2001/058* (2013.01); *A61N 2001/0585* (2013.01)

(58) Field of Classification Search
CPC .... A61N 1/0592; A61N 1/372; A61N 1/059; A61N 1/3624; A61N 1/3756; A61N 1/37205; A61N 1/05; A61N 1/0587; A61B 17/3468; A61B 2017/00243
See application file for complete search history.

(56) References Cited

U.S. PATENT DOCUMENTS

| | | |
|---|---|---|
| 3,835,864 A | 9/1974 | Rasor et al. |
| 4,471,777 A | 9/1984 | McCorkle, Jr. |

(Continued)

OTHER PUBLICATIONS

U.S. Appl. No. 14/039,937, filed Sep. 27, 2013, Ronan Wood, et al. (Unpublished).

(Continued)

*Primary Examiner* — Tuan V Nguyen
*Assistant Examiner* — Kevin Everage
(74) *Attorney, Agent, or Firm* — Evans M. Mburu

(57) ABSTRACT

Delivery tools of interventional medical systems facilitate deployment of relatively compact implantable medical devices that include sensing extensions, for example, right ventricular cardiac pacing devices that include a sensing extension for atrial sensing. An entirety of such a device is contained within a delivery tool while a distal-most portion of the tool is navigated to a target implant site; the tool is configured to expose, out from a distal opening thereof, a distal portion of the device for initial deployment, after which sensing, via a sense electrode of the aforementioned sensing extension of the device, can be evaluated without withdrawing the tool from over the remainder of the device that includes the sensing extension.

10 Claims, 8 Drawing Sheets

(51) Int. Cl.
  *A61B 18/00* (2006.01)
  *A61N 1/375* (2006.01)
  *A61N 1/05* (2006.01)

(56) References Cited

U.S. PATENT DOCUMENTS

| | | | |
|---|---|---|---|
| 4,886,065 A | 12/1989 | Collins, Jr. | |
| 7,519,424 B2 | 4/2009 | Dennis et al. | |
| 8,504,156 B2 | 8/2013 | Bonner et al. | |
| 8,527,068 B2 | 9/2013 | Ostroff | |
| 8,634,912 B2 | 1/2014 | Bornzin et al. | |
| 8,634,919 B1 | 1/2014 | Hou et al. | |
| 8,670,842 B1 | 3/2014 | Bornzin et al. | |
| 9,283,382 B2 * | 3/2016 | Berthiaume | A61N 1/0587 |
| 2006/0085041 A1 | 4/2006 | Hastings et al. | |
| 2013/0023975 A1 | 1/2013 | Locsin | |
| 2013/0035748 A1 | 2/2013 | Bonner et al. | |
| 2013/0103047 A1 * | 4/2013 | Steingisser | A61N 1/3756 606/129 |
| 2013/0110219 A1 | 5/2013 | Bornzin et al. | |
| 2013/0116740 A1 | 5/2013 | Bornzin et al. | |
| 2014/0107723 A1 | 4/2014 | Hou et al. | |

OTHER PUBLICATIONS (PCT/US2015/040266) PCT Notification of Transmittal of the International Search Report and the Written Opinion of the International Searching Authority, Mailed Oct. 8, 2015, 12 pages.

* cited by examiner

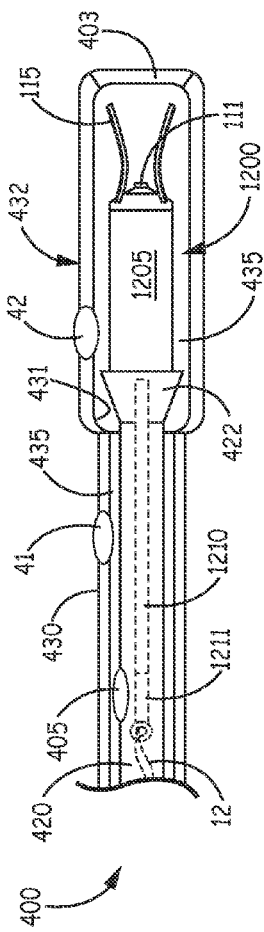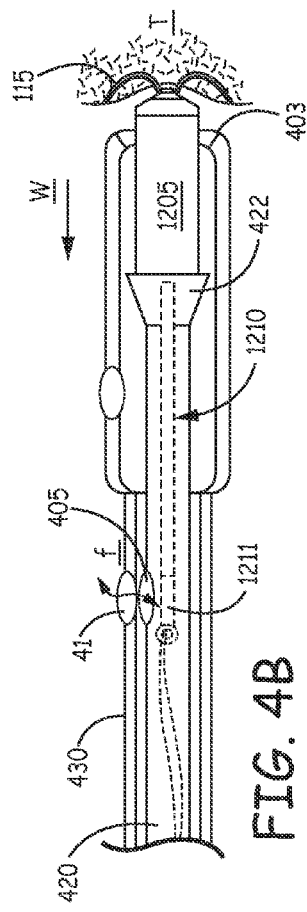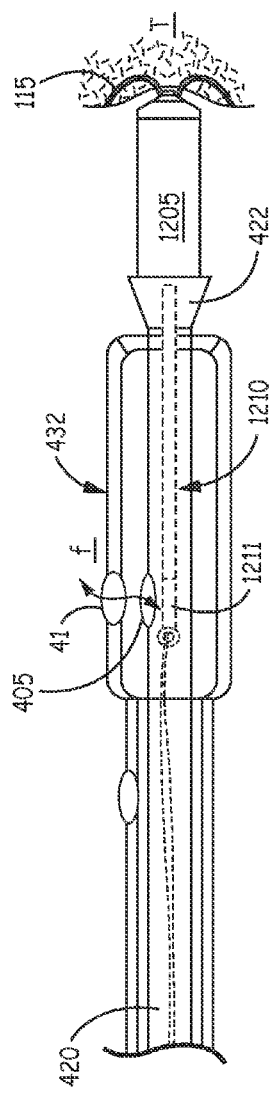

INTERVENTIONAL MEDICAL SYSTEMS, TOOLS, AND METHODS OF USE

CROSS-REFERENCE TO RELATED APPLICATIONS

The present application claims priority to United States Provisional patent application having the Ser. No. 62/025,620, which was filed on Jul. 17, 2014, and to United States Provisional patent application having the Ser. No. 62/041,927, which was filed on Aug. 26, 2014, both of which are hereby incorporated by reference in their entireties. The present application is related to the commonly assigned U.S. patent application Ser. No. 14/518,027, which is filed concurrently herewith and entitled the same, and which is incorporated by reference in its entirety.

FIELD OF THE DISCLOSURE

The present invention pertains to interventional medical systems, and more particularly to tools and associated methods configured to facilitate percutaneous transvenous deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, like a device 100, which is shown in FIG. 1, implanted within the right ventricle RV of the heart. FIG. 1 illustrates device 100 having been deployed out from a distal portion of a standard guiding catheter 150, which has been maneuvered up through the inferior vena cava IVC and into the right ventricle RV from the right atrium RA, according to methods known in the art of interventional cardiology. With further reference to FIG. 1, an hermetically sealed housing 105, preferably formed from a biocompatible and biostable metal such as titanium, contains a pulse generator, or an electronic controller (not shown), to which an electrode 111 is coupled, for example, by an hermetic feedthrough assembly (not shown) like those known to those skilled in the art of implantable medical devices. FIG. 1 further illustrates device 100 including a fixation member 115, which engages tissue at the implant site to secure device 100 thereto so that electrode 111 is held in intimate contact with the tissue at the site. Housing 105 may be overlaid with an insulative layer, for example, medical grade polyurethane, parylene, or silicone, and a portion of housing 105 from which the insulative layer is removed, may be employed as another electrode to function in conjunction with electrode 111 for ventricular bipolar pacing and sensing.

SUMMARY

Delivery tools of interventional medical systems disclosed herein facilitate deployment of relatively compact implantable medical devices that include sensing extensions, for example, right ventricular cardiac pacing devices that include a sensing extension for atrial sensing. According to embodiments and methods of the present invention, an entirety of such a device is contained within a delivery tool, while a distal-most portion of the tool is navigated to a target implant site; the tool is configured to expose, out from a distal opening thereof, a distal portion of the device for initial deployment (e.g., engagement of a device fixation member with tissue at the site), after which sensing, via a sense electrode of the aforementioned sensing extension of the device, can be evaluated without withdrawing the tool from over the remainder of the device that includes the sensing extension.

According to some embodiments, the aforementioned delivery tool includes a handle, an elongate inner member, and an elongate deployment tube, which includes a lumen in which the inner member extends, and the deployment tube is moveable with respect to the inner member, for example, via a control member of the handle; the inner member has a lumen to accommodate the sensing extension of the aforementioned device, when a proximal end of a housing of the device abuts a distal end of the inner member, and the lumen of the deployment tube, along a length of a distal-most portion of the deployment tube, is sized to contain an entirety of the device housing, along with the distal end of the inner member that abuts a proximal end of the housing, for deployment of the device out through a distal opening of the lumen of the deployment tube. The embodiments of the delivery tool further include an inner conductive feature, which is formed in the inner member, in proximity to the distal end thereof, and an outer conductive feature, which is formed in the deployment tube, either in proximity to, or along the distal-most portion thereof, wherein the inner conductive feature is configured to provide a conductive pathway between the sense electrode of the aforementioned sensing extension of the device and the outer conductive feature, and the outer conductive feature is configured to provide a conductive pathway between the inner conductive feature and a location outside the deployment tube, for example, when the inner and outer conductive features are approximately aligned with one another, for example, via movement of the deployment tube with respect to the inner member. The inner and outer conductive features may be defined by apertures that provide conduction via fluid communication between the sense electrode of the sensing extension and the location outside the deployment tube, wherein a saline flush through the lumen of the inner member and through the apertures can create the conductive pathway. Or, according to some alternate embodiments, each of the inner and outer conductive features is formed by an electrically conductive segment of the inner member and the deployment tube, respectively. In some embodiments these segments are configured to come into direct electrical contact with one another, when aligned with one another, and thereby create the conductive pathway; whereas, in some alternate embodiments saline flushed through the lumens of the inner member and the deployment tube in conjunction with the electrically conductive segments create the conductive pathway, and direct electrical contact between the segments is not necessary.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIGS. 4A-C are partial cut-away section views of a distal portion of an interventional medical system that includes a delivery tool, like the tool of FIGS. 3A-B, according to some embodiments and methods;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
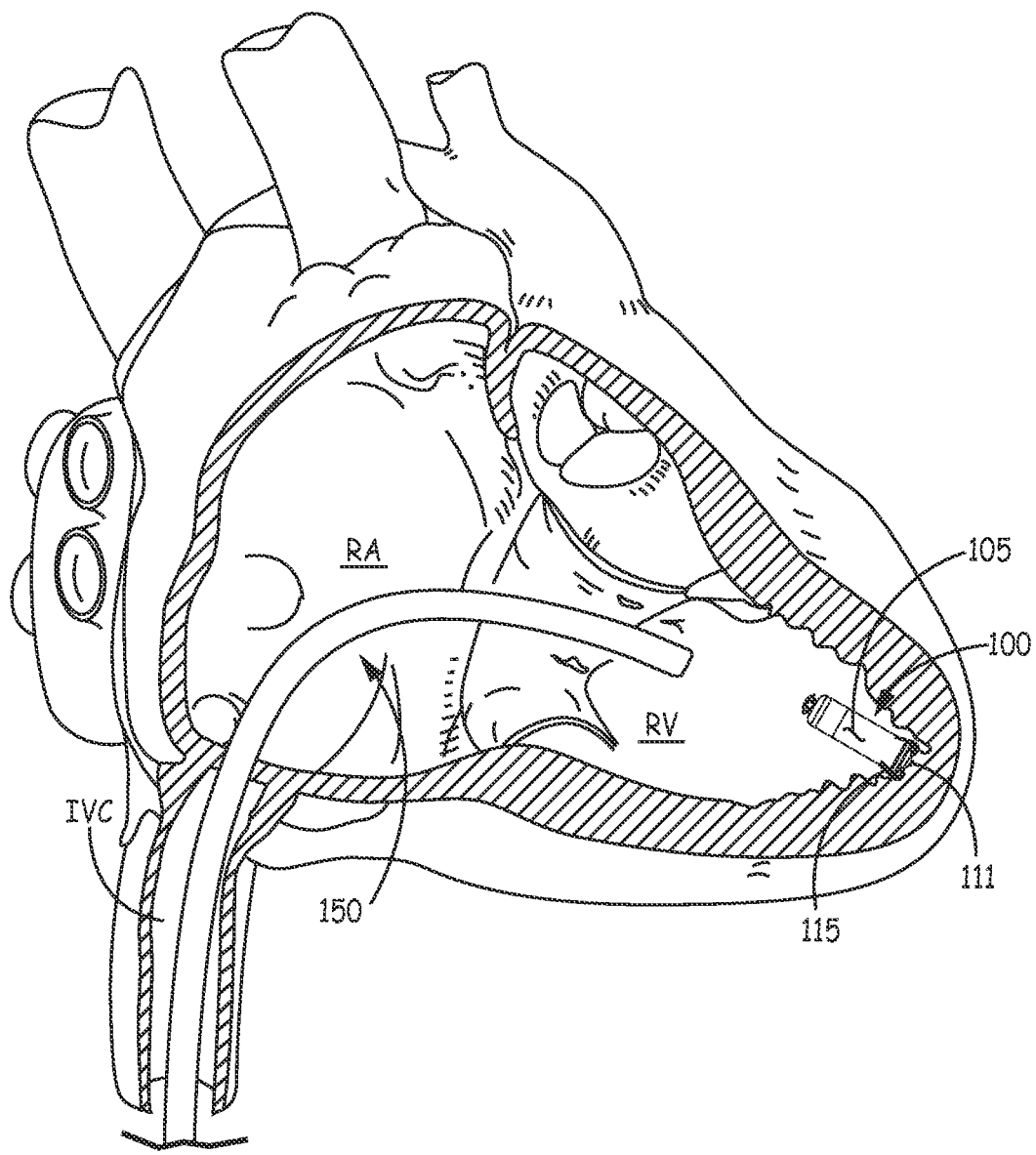
FIG. 1 is a schematic showing an exemplary interventional medical system for cardiac stimulation.
Figure 2A:
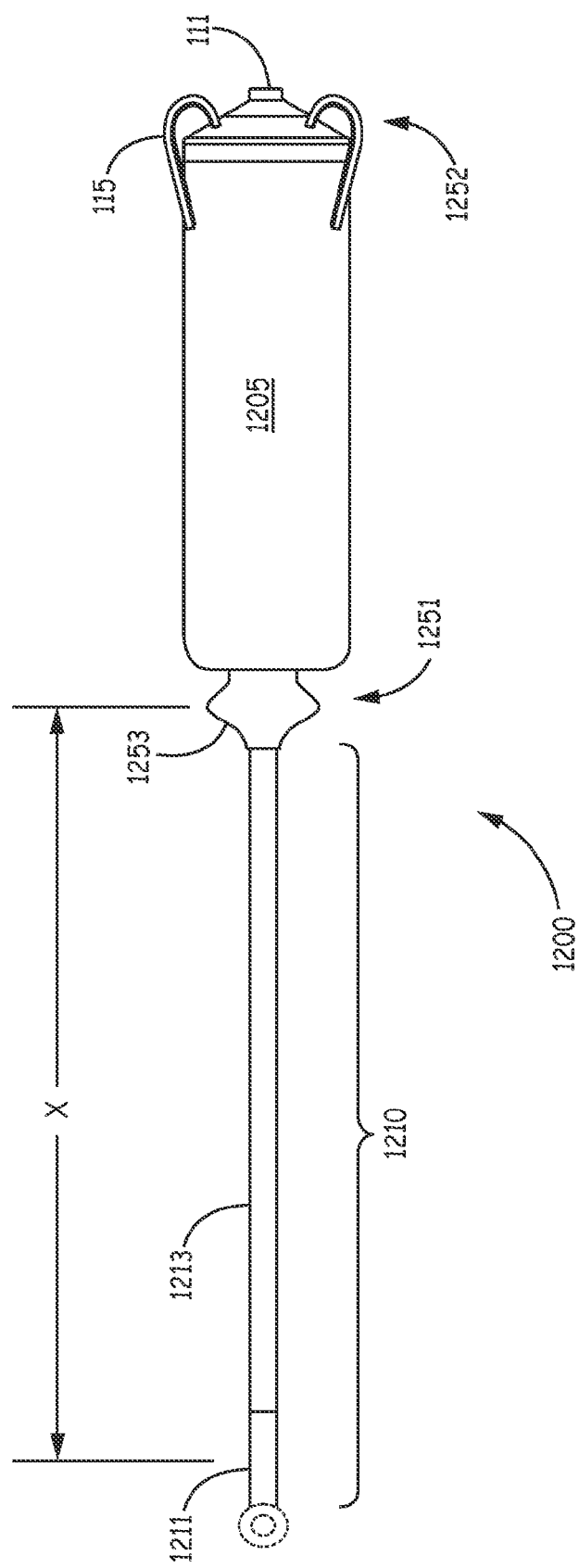
FIG. 2A is a plan view of an exemplary implantable medical device, which may be employed by systems of the present invention.
Figure 2B:
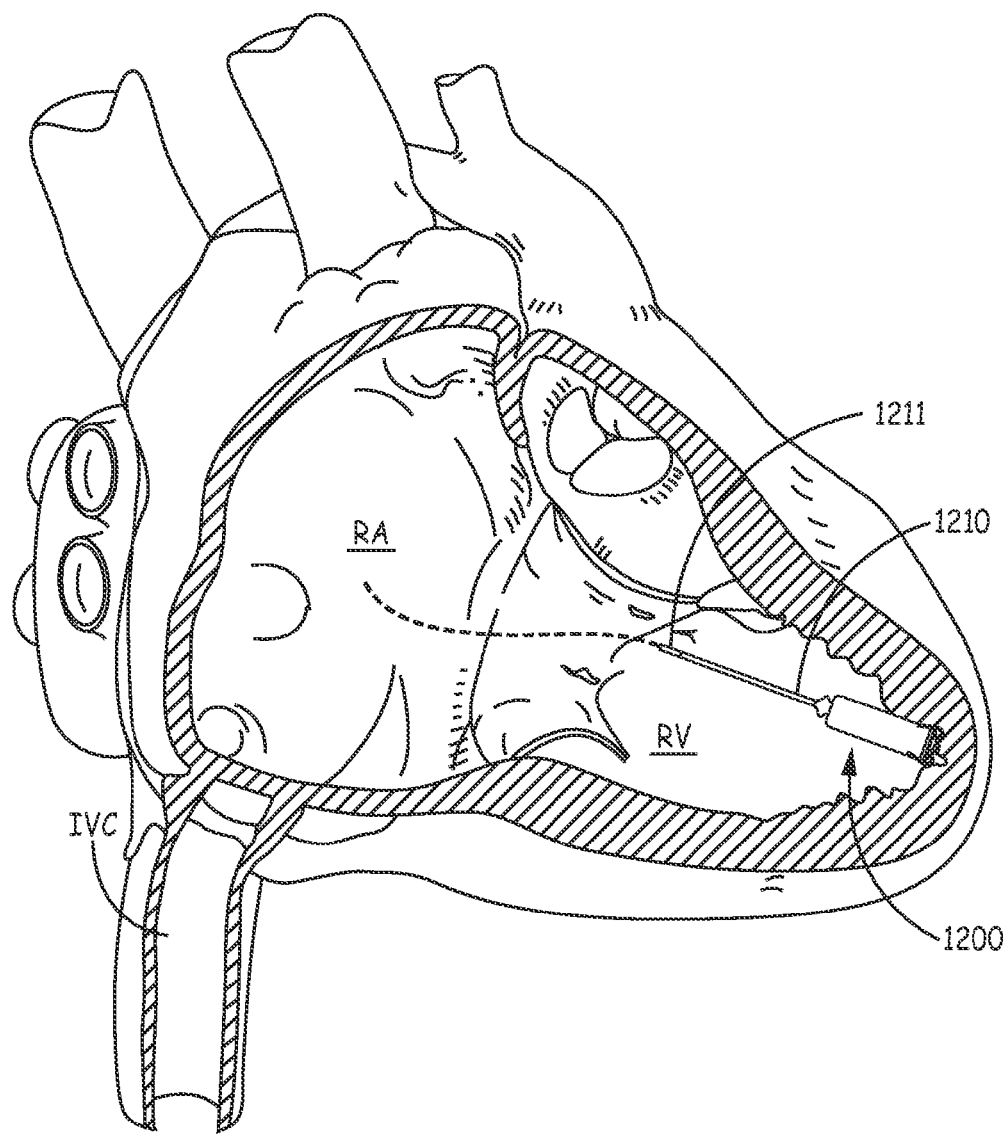
FIG. 2B is a schematic showing the exemplary device of FIG. 2A implanted in a right ventricle.

FIG. 2A is a plan view of an exemplary implantable medical device 1200, which may be employed in systems of the present invention, for example, those described below in conjunction with FIGS. 3-6B. FIG. 2A illustrates device 1200 including an hermetically sealed housing 1205, cardiac pacing and sensing electrodes 111, 1211, and fixation member 115 coupled to a distal end 1252 of device housing 1205. Like the above described housing 105 of device 100 (FIG. 1), housing 1205 of device 1200 contains a power source and an electronic controller (not shown) within a relatively compact form factor, wherein electrode 111 is coupled to the controller via an hermetically sealed feedthrough assembly known in the art. Fixation member 115, like in device 100, holds electrode 111 in intimate contact with tissue at an implant site, for example, as illustrated in FIG. 2B. With further reference to FIG. 2A, unlike device 100, device 1200 includes a sensing extension 1210 on which sense electrode 1211 is mounted.

Sensing extension 1210 extends proximally from a proximal end 1251 of device housing 1205, such that sense electrode 1211 is spaced a distance X from proximal end 1251 of housing 1205. The distance X locates sense electrode 1211 for atrial sensing (P-waves), when device 1200 is implanted in the right ventricle RV, for example, as shown in FIG. 2B. The distance X may be between approximately 6 cm and approximately 10 cm, such that electrode 1211 is located in the right ventricle RV, as shown; or, according to alternate embodiments, distance X may be between approximately 10 cm and approximately 15 cm, such that electrode is located in the right atrium RA, for example, as indicated with the dashed line in FIG. 2B. According to the illustrated embodiment, sensing extension 1210 includes an insulated conductor 1213, for example, a coiled medical grade stainless steel or MP35N wire disposed within a medical grade silicone or polyurethane jacket, which is electrically coupled to device housing 1205, for example, via a crimp or a weld. A co-pending and commonly assigned U.S. patent application Ser. No. 62/025,690 provides a detailed description of an implantable medical device similar to device 1200, the description of which is hereby incorporated by reference.

Figure 3A:
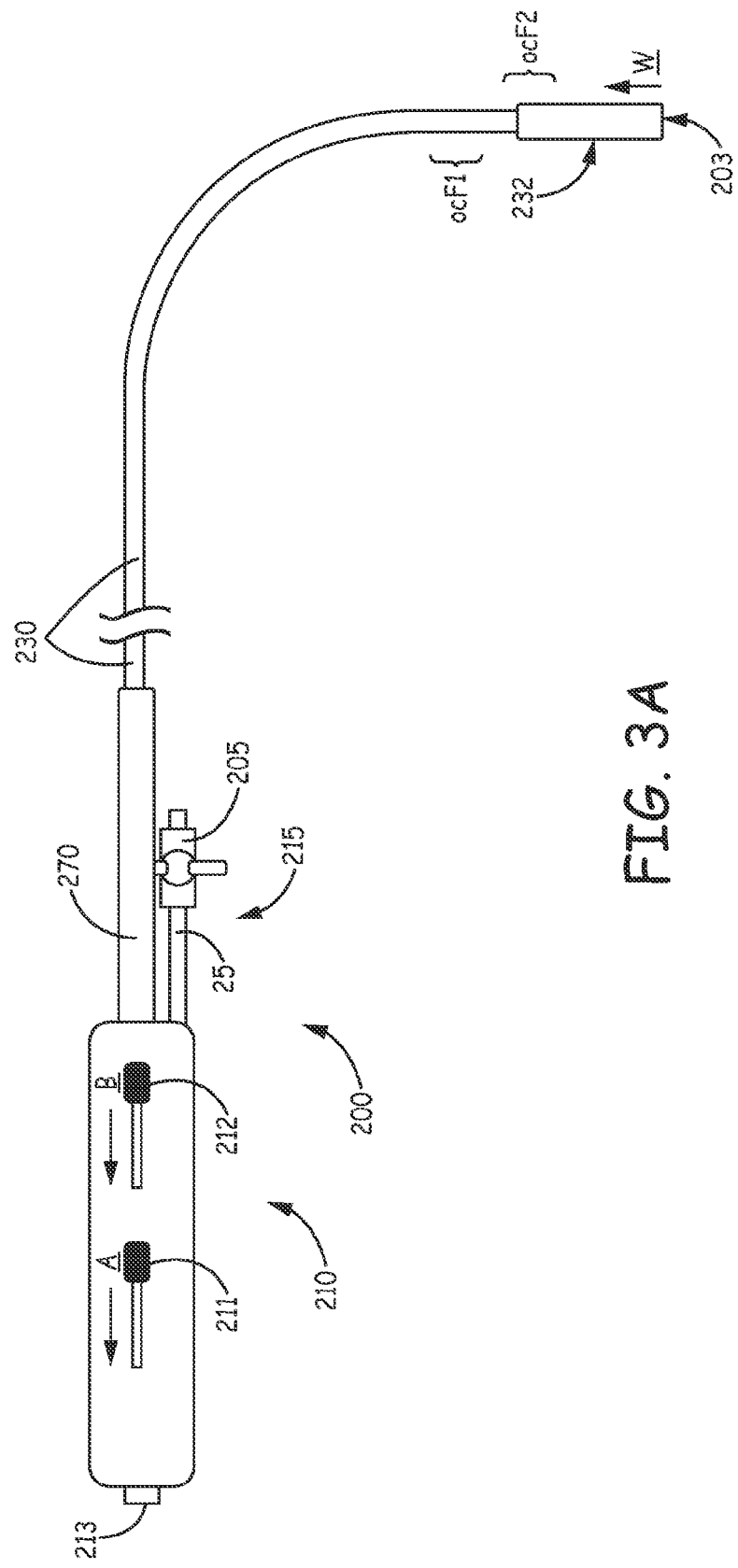
FIG. 3A is a plan view of a delivery tool, according to some embodiments of the present invention.
Figure 3B:
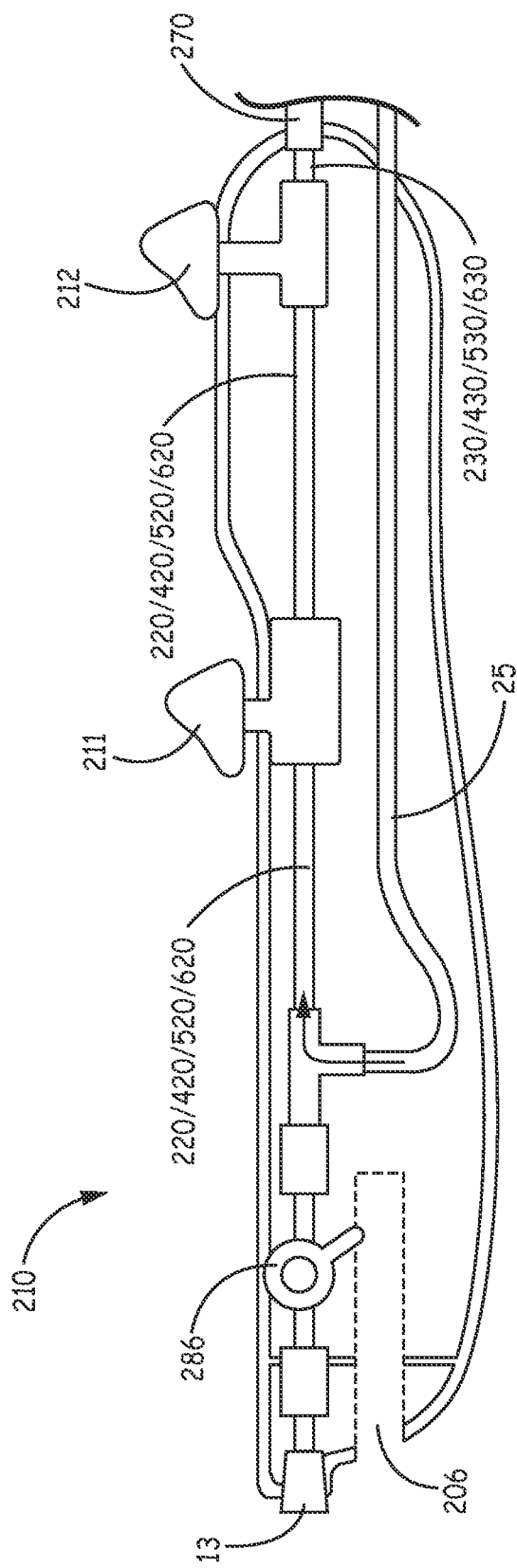
FIG. 3B is a longitudinal cross-section view through a handle of the tool of FIG. 3A, according to some embodiments.

FIG. 3A is a plan view of a delivery tool 200 that may be included together with device 1200 in an interventional medical system, according to some embodiments. FIG. 3A illustrates tool 200 including a handle 210, and an outer assembly, which is formed by an elongate deployment tube 230 and an outer, stabilizing sheath 270 that surrounds a proximal portion of deployment tube 230 in proximity to handle 210. FIG. 3B is a longitudinal cross-section view through handle 210, in which a proximal end of sheath 270 is shown secured to handle 210, and a proximal end of deployment tube 230 is shown coupled to a control member 212 of handle 210 such that tube 230 is moveable, via control member 212, relative to sheath 270, according to some embodiments. With further reference to FIG. 3B, tool 200 also includes an elongate inner member 220, which extends within a lumen of deployment tube 230 and an entirety of deployment tube 230 is also movable with respect to the inner member 220, via control member 212. Inner member 220 includes a distal end (not shown), which is located within a distal-most portion 232 of deployment tube 230 and is configured to engage an implantable medical device by abutting an end of the device, for example, proximal end 1251 of device 1200. FIGS. 3A-B further illustrate tool 200 including a flushing subassembly 215 coupled to handle 210, wherein subassembly 215 includes a tube 25 defining a flush lumen, which extends between a connector port 205 (e.g., a stopcock type fitting) and one or more lumens of inner member 220. The arrow in FIG. 3B indicates the flow of a flushing fluid (e.g., saline) from the flush lumen to the one or more lumens of inner member 220, and, although not shown, inner member 220 may include one or more ports formed in the sidewall thereof to allow the flushing fluid to flow through the lumen of deployment tube 230 as well.

With further reference to FIG. 3A, the lumen of deployment tube 230, along a length of distal-most portion 232, is sized to contain the distal end of inner member 220 along with the entirety of device housing 1205; and a lumen (not shown) of inner member 220, which extends proximally from an opening terminating the distal end of inner member 220, is sized to accommodate sensing extension 1210 of device 1200, when the distal end of inner member 220 abuts proximal end 1251 of device housing 1205. Thus a distal portion of tool 200, with an entirety of device 1200 contained therein, may be navigated to a target implant site, for example, in the right ventricle RV by advancing tool 200 through a venous system of the patient, for example, from a femoral venous access site and up through the inferior vena cava IVC (FIG. 2B). A length of deployment tube 230, between handle 210 and distal opening 203 of deployment tube 230, when tube 230 is in the position shown in FIG. 3A, may be between approximately 103 cm and approximately 107 cm, for example, to reach the right ventricle RV from the femoral access site. According to some embodiments of the present invention, delivery tool 200 includes articulating features to facilitate the navigation of the distal portion of delivery tool 200 to the target implant site; for example, inner member 220 of delivery tool 200 may include a pull wire (not shown) integrated therein and coupled to another control member 211 of handle 210 that, when moved per arrow A, causes inner member 220 and deployment tube 230 to bend along distal portions thereof. Suitable construction detail for a delivery tool like tool 200 is described in co-pending and commonly assigned U.S. patent application Ser. No. 14/039,937, the description of which is hereby incorporated by reference.

Once tool 200 is located so that a distal opening 203 (FIG. 3A) of the lumen of deployment tube 230 is located adjacent to the implant site, control member 212 may be moved, per arrow B, to withdraw deployment tube 230, per arrow W, and expose fixation member 115 (FIG. 2A) of device 1200 for engagement with tissue at the target site. When fixation member 115 is engaged such that electrode 111 is in intimate contact with the tissue, pacing and sensing performance of device 1200 may be evaluated without having to withdraw delivery tool 200 proximally from device 1200 to expose a remainder of device 1200, because, according to embodiments of the present invention, tool 200 includes conductive features for creating a conductive pathway between sense electrode 1211 of device sensing extension 1210 and a location outside tool 200 (e.g., the blood pool of the patient's venous system), while sensing extension 1210 is still contained within inner member 220 and deployment tube 230. FIG. 3A illustrates potential locations of one or more outer conductive features ocF1, ocF2 of deployment tube 230, which work in conjunction with inner conductive features of inner member 220 to create the conductive pathway, according to various embodiments described below.

FIGS. 4A-C are partial cut-away section views of a distal portion of an interventional medical system that includes a delivery tool 400, which is similar, in some respects, to delivery tool 200, according to some embodiments and methods of the present invention. FIGS. 4A-C illustrate tool 400 including an inner member 420 and a deployment tube 430, wherein inner member 420 extends within a lumen 435 of tube 430, and tube 430 is movable with respect to inner member 420, for example, via a control member of a handle of tool 400, for example, control member 212 of handle 210 (FIG. 3B). FIG. 4A shows and entirety of device 1200 contained within the distal portion of tool 400, with device housing 1205, electrode 111, and fixation member 115 all located in a distal-most portion 432 of deployment tube 430, and with housing 1205 abutting a distal end 422 of inner member 420 so that sensing extension 1210 of device 1200 (shown with dashed lines) extends within a lumen of inner member 420. According to an exemplary embodiment, distal-most portion 432 has a length of approximately 3.5 cm (~1.4 inch), an inner diameter of approximately 0.275 inch (~0.7 cm), and an outer diameter of approximately 0.3 inch (~0.8 cm). Distal end 422 of inner member 420 is shown being enlarged relative to a remainder of inner member 420 and thus constrained from moving proximally out of distal-most portion 432 by a shoulder 431 of distal-most portion 432, according to some embodiments. Although not shown, it should be understood that the lumen of inner member 420 extends proximally from an opening thereof that terminates distal end 422 of inner member 420, and, according to an exemplary embodiment, the lumen of inner member 420 has a diameter between approximately 1.8 mm (0.070 inch) and approximately 2.4 mm (0.095 inch), to accommodate sensing extension 1210 extending therein. According to some embodiments, the lumen of inner member 420 extends to a proximal end of inner member 420, for example, which is located within handle 210 of tool 400; according to some alternate embodiments, inner member 420 includes a multi-lumen length extending from the proximal end of inner member 420 to the above-described portion of the lumen that accommodates device sensing extension 1210.

FIGS. 4A-C further illustrate deployment tube 430 including outer conductive features 41, 42, and inner member 420 including an inner conductive feature 405, wherein conductive features 41, 42, 405 are defined by apertures formed through a wall of deployment tube 430 and a wall of inner member 420, respectively. According to the illustrated embodiment, inner conductive feature 405 is located to provide a conductive pathway, via fluid communication, between sense electrode 1211 of device extension 1210 and one of outer conductive features 41, 42 of deployment tube 430, when aligned therewith, as shown in FIG. 4B or FIG. 4C. With reference to FIG. 4B, when an operator initially retracts/withdraws deployment tube 430, per arrow W, to expose fixation member 115 out through a distal opening 403 of lumen 435 of tube 430, and has pushed inner member 420 to engage fixation member 115 with tissue T at an implant site, outer conductive feature 41, which is located proximal to distal-most portion 432 of tube 430, is approximately aligned with inner conductive feature 405 to allow conduction via fluid communication between the blood pool outside deployment tube 430 and sense electrode 1211. A saline flush, for example, injected at connector port 205 (described above in conjunction with FIGS. 3A-B), through the lumen of inner member 420, and through features 41, 405 can create a conductive pathway, per double-headed arrow f, which allows the operator to evaluate sensing via sense electrode 1211, for example, the sensing of atrial activity (e.g., P-waves) when the implant site is in the right ventricle RV. With reference to FIG. 4C, when the operator retracts deployment tube 430 farther, so that distal end 422 of inner member 420 and device housing 1205 are both exposed outside tool 400, outer conductive feature 42, which is located along distal-most portion 432 of tube 430, is aligned with inner conductive feature 405 to also allow fluid communication that creates the conductive pathway, per arrow f, thereby allowing the aforementioned sensing evaluation. In the absence of the aforementioned saline flush, blood flow into lumen 435 of deployment tube 430, through one or both of features 41, 42, and then into the lumen of inner member 420, through feature 405, can create a sufficient conductive pathway. Each conductive feature 41, 42, 405 may include a single aperture or a plurality of apertures, for example, formed about a perimeter of the respective wall. Although FIGS. 4A-C illustrate deployment tube 430 including two outer conductive features 41, 42, according to some alternate embodiments, deployment tube 430 includes only one of outer conductive features 41, 42.

Figure 5A:
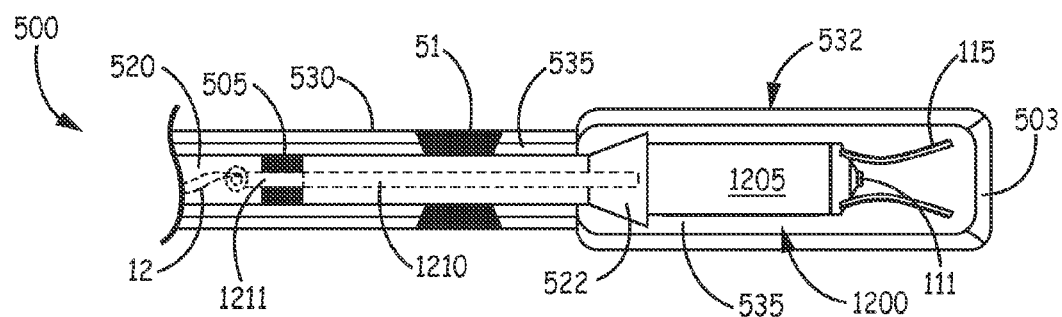
FIGS. 5A-B are partial cut-away section views of a distal portion of an interventional medical system that includes a delivery tool, like the tool of FIGS. 3A-B, according to some alternate embodiments and methods.
Figure 5B:
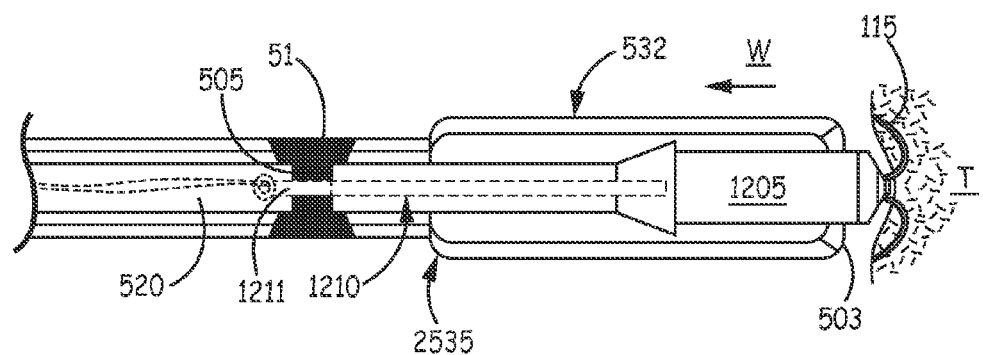

FIGS. 5A-B are partial cut-away section views of a distal portion of an interventional medical system that includes a delivery tool 500, according to some alternate embodiments and methods. Like delivery tool 400, FIG. 5A illustrates tool 500 including an inner member 520 and a deployment tube 530, wherein inner member 520 extends within a lumen 535 of tube 530, and tube 530 is movable with respect to inner member 520, for example, via a control member of a handle of tool 500, for example, control member 212 of handle 210 (FIG. 3B). Also like tool 400, FIG. 5A shows device 1200 contained in a distal-most portion 532 of tube 530 with device housing 1205 abutting a distal end 522 of inner member 520, and with device sensing extension 1210, again shown with dashed lines, extending within a lumen of inner member 520, wherein the lumen is similar to that of inner member 420 described above. FIGS. 5A-B further illustrate deployment tube 530 including an outer conductive feature 51, and inner member 520 including an inner conductive feature 505, wherein conductive features 51, 505 are defined by electrically conductive segments of a wall of deployment tube 530 and a wall of inner member 520, respectively. According to the illustrated embodiment, when sensing extension 1210 extends within the lumen of inner member 520, as shown, electrode 1211 of sensing extension 1210 may interface with inner conductive feature 505 to make electrical contact therewith; and, with reference to FIG. 5B, when an operator initially retracts/withdraws deployment tube 530, per arrow W, to expose device fixation member 115 out through a distal opening 503 of lumen 535 of tube 530, and has pushed inner member 520 to engage fixation member 115 with tissue T at an implant site, outer conductive feature 51, for example, located proximal to distal-most portion 532 of tube 530, is aligned with inner conductive feature 505 to make electrical contact therewith. An outer surface of outer conductive feature 51 is in conductive contact with the blood pool outside tool 500, so that the aligned conductive features 51, 505, for example, as illustrated in FIG. 5B, provide a conductive pathway between the interfacing sense electrode 1211 and the blood pool, which allows the operator to evaluate sensing via sense electrode 1211, for example, the sensing of atrial activity (e.g., P-waves) as described above, without having to withdraw tool 500 from over an entirety of device 1200.

The interfaces between sense electrode 1211 and inner conductive feature 505, and between inner conductive feature 505 and outer conductive feature 51 may be ones of direct electrical contact, or simply through conductors where direct contact is not required; in either case features 505, 51 provide the conductive pathway between sense electrode 1211 and the blood pool outside tube 530. The electrically conductive segments of inner and outer conductive features 505, 51, according to some embodiments, are formed by a conductive material dispersed within the walls of inner member 520 and deployment tube 530, for example, being in the form of a woven braid of electrically conductive strands, such as fine stainless steel wire, integrated into the walls, wherein, a bulk of each wall may be formed from a polyether block amide. According to some alternate embodiments, the conductive segments of inner and outer conductive features 505, 51 are formed by electrically conductive inserts joined to the walls of inner member 520 and deployment tube 530, for example, stainless steel rings.

With reference back to FIGS. 2A-B, inner conductive feature 405, 505 of each tool 400, 500 is located relative to distal end 422, 522 of the corresponding inner member 420, 520 to either accommodate a length of sensing extension 1210 in which distance X is between approximately 6 cm and approximately 10 cm, such that electrode 1211 is located in the right ventricle RV, or to accommodate a longer length of sensing extension 1210 in which distance X is between approximately 10 cm and approximately 15 cm, such that electrode is located in the right atrium RA.

For any of the above-described embodiments, if the operator finds that the sensing is adequate, after the operator has retracted deployment tube 430, 530 relative to inner member 420, 520 and device 1200, engaged fixation member 115 of device 1200 at the target implant site in the right ventricle RV, and evaluated atrial sensing via the conductive pathway formed by the corresponding inner and outer conductive features, the operator may withdraw tool 400, 500 from over an entirety of the implanted device 1200. With further reference to FIG. 2A, an optional eyelet feature terminating a proximal end of sensing extension 1210 is shown with dashed lines. The optional eyelet feature is useful for attaching a tether 12 (shown with dashed lines in FIGS. 4A and 5A) to device 1200, while the device is loaded in tool 400, 500 and during the deployment of device 1200 out from tool 400, 500. With reference to FIG. 3B, tether 12 may extend within the lumen of inner member 420, 520 and out from a proximal opening 13 thereof, so that the operator may have access to the tether in proximity to handle 210. With further reference to FIG. 3B, a proximal end of tether 12 may be attached to a holder (not shown) that fits within a receptacle 206 of handle 210, and a valve member 286 of handle 210 (e.g., a stopcock type valve) may be configured to alternately secure and release tether 12 within the lumen of inner member 420, 520. After fixation member 115 is engaged at the implant site, the operator may open valve member 286 to release tether 12, grasp the tether holder, and tug with tether 12 on device 1200 to test the engagement of fixation member 115 or to disengage fixation member 115, if the operator has determined that it is necessary to reposition device 1200 at another implant site.

Figure 6A:
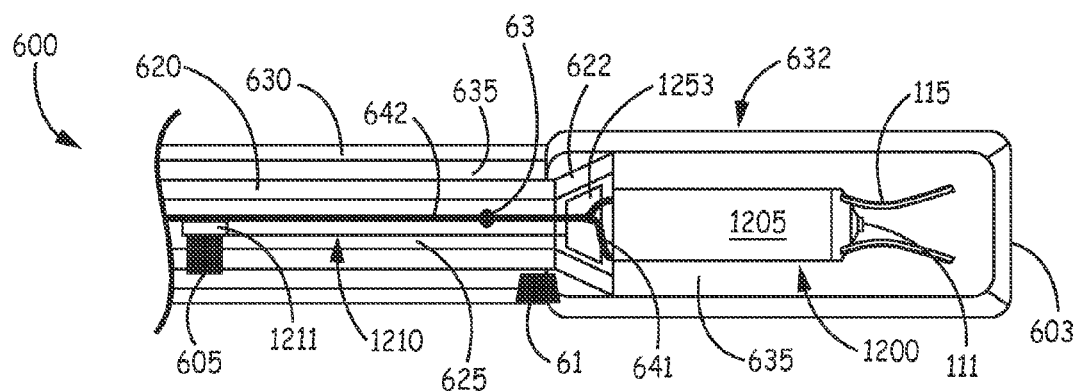
FIG. 6A is a cross-section view through a distal portion of yet another delivery tool employed by an interventional medical system, according to some embodiments.
Figure 6B:
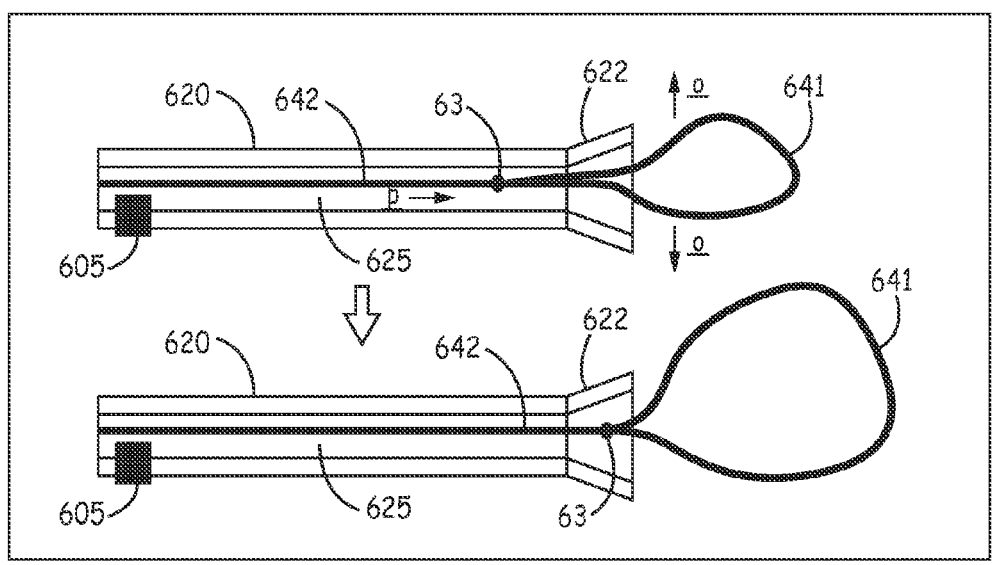
FIG. 6B is a schematic demonstrating an opening operation of a snare member of the tool shown in FIG. 6A, according to some methods of the present invention.

According to some alternate embodiments, rather than employing tether 12, interventional medical systems of the present invention may employ a snare member, for example, as illustrated in FIGS. 6A-B. FIG. 6A is a cross-section view through a distal portion of yet another delivery tool 600; and FIG. 6B is a schematic demonstrating an opening operation of a snare member of tool 600, according to some methods of the present invention. FIG. 6A illustrates tool 600, like tools 400, 500, including an inner member 620 and a deployment tube 630, wherein inner member 620 extends within a lumen 635 of tube 630, and tube 630 is movable with respect to inner member 620, as described above for tools 400, 500, for example, via a control member of a handle of tool 600, for example, control member 212 of handle 210 (FIGS. 3A-B). Also like tools 400, 500, FIG. 6A shows device 1200 contained in a distal-most portion 632 of tube 630 with device housing 1205 abutting a distal end 622 of inner member 620, and with device sensing extension 1210, extending within a lumen 625 of inner member 620 such that sense electrode 1211 interfaces with an inner conductive feature 605 of inner member 620. FIG. 6A further illustrates the snare member of delivery tool 600 including an elongate shaft 642 and a loop 641 coupled to a distal end of shaft 642 at a junction 63. Snare member shaft 642 extends alongside sensing extension 1210 within lumen 625 of inner member 620, and loop 641 is closed around a snare attachment feature 1253 of device housing 1205 (feature 1253 also seen in FIG. 2A), when junction 63 of the snare member is located within lumen 625, as shown in FIG. 6A, so that a majority of loop 641 is constrained within lumen 625.

According to the illustrated embodiment, the snare member is slideably engaged within lumen 625, but a proximal segment of shaft 642 may be secured against sliding by valve member 286 of handle 210 (FIG. 3B) to keep loop 641 closed around feature 1253 of device 1200 while an operator navigates distal-most portion 632 of delivery tool 600, with device 1200 contained therein, to a target implant site (e.g., in the right ventricle RV), and while the operator retracts deployment tube 630 relative to inner member 620 and device 1200 and engages fixation member 115 of device 1200 at the target implant site by pushing on inner member 620. FIG. 6A further illustrates deployment tube 630 of delivery tool 600 including an outer conductive feature 61 located at a proximal end of distal-most portion 632, so that, when deployment tube 630 is retracted to expose device fixation member 115 for engagement with tissue at the target implant site, inner conductive feature 605 of inner member 620 comes into electrical contact with outer conductive feature 61 to provide a conductive pathway between sense electrode 1211, interfacing with inner conductive feature 605, and a location outside deployment tube 630, for example, the blood pool in the right ventricle RV. Thus, sensing via electrode 1211 may be evaluated, via the conductive pathway, without having to withdraw tool 600 from over an entirety of device 1200. According to some embodiments, as illustrated, inner and outer conductive features 605, 61 are formed by electrically conductive segments, for example, integrated into the walls of inner member 620 and deployment tube 630, respectfully, according to any of the embodiments described above. According to some alternate embodiments, inner and outer conductive features 605, 61 may be defined by apertures formed through a wall of inner member 620 and a wall of deployment tube 630, respectively, to provide conduction via fluid communication between sense electrode 1211 and the blood pool outside deployment tube 630, as described above for delivery tool 400.

Following the evaluation of sensing via electrode 1211, and if adequate sensing is confirmed, the operator may release device 1200 from the snare member. With reference to FIG. 6B, the snare member is released when the operator advances, or pushes shaft 642 of the snare member distally, per arrow p, to open snare loop 641, per arrows o. According to some methods, prior to releasing device 1200 from the snare member, the operator can test fixation of the engaged fixation member 115 by applying a tug force to snare shaft 642; also, the operator can employ the snare member, with snare loop 641 closed around device attachment feature 1253, to disengage fixation member 115, if the operator has determined that it is necessary to reposition device 1200 at another implant site.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising:
an implantable medical device comprising an electronic controller, an hermetically sealed housing containing the controller, and a sensing extension coupled to the controller, the extension extending externally from a proximal end of the housing, the extension including a sense electrode;
a delivery tool facilitating deployment of the device, the tool comprising:
a handle including a control member;
an elongate inner member including a proximal end secured to the handle, a distal end, an inner conductive feature located in proximity to the distal end of the inner member, and a lumen extending proximally from an opening thereof that terminates the distal end of the inner member, the distal end of the inner member being configured to abut the proximal end of the device housing, and the lumen being sized to accommodate the extension of the device, when the distal end of the inner member abuts the proximal end of the device, such that the sense electrode interfaces with the inner conductive feature; and an elongate deployment tube including a proximal end coupled to the control member of the handle, a distal-most portion, a lumen extending from an opening thereof at the proximal end of the deployment tube to another opening thereof that terminates the distal-most portion at a distal end thereof, and an outer conductive feature located along or in proximity to the distal-most portion, the inner member extending within the lumen of the deployment tube, an entirety of the deployment tube being longitudinally moveable with respect to the inner member by means of the control member of the handle, and the lumen of the deployment tube, along a length of the distal-most portion, being sized to contain the distal end of the inner member together with an entirety of the device housing; and wherein the inner conductive feature of the inner member is configured to provide a conductive pathway between the interfacing sense electrode of the sensing extension of the device and the outer conductive feature of the deployment tube, and the outer conductive feature of the deployment tube is configured to provide a conductive pathway between the inner conductive feature and a location outside the deployment tube, when the inner and outer conductive features are approximately aligned with one another via movement of the deployment tube with respect to the inner member.

2. The system of claim 1, wherein each of the inner and outer conductive features of the tool comprises one or more apertures providing conduction via fluid communication between the location outside the deployment tube and the sense electrode of the device extension, when the lumen of the inner member of the tool accommodates the extension and the distal end of the inner member abuts the proximal end of the device housing, and when the inner and outer conductive features are approximately aligned.

3. The system of claim 1, wherein:
the inner conductive feature of the tool comprises an electrically conductive segment of the inner member of the tool, the conductive segment of the inner member being in electrical contact with the sense electrode of the device extension, when the lumen of the inner member accommodates the extension and the distal end of the inner member abuts the proximal end of the device housing; and
the outer conductive feature of the tool comprises an electrically conductive segment of the deployment tube of the tool, the conductive segment of the deployment tube being in electrical contact with the conductive segment of the inner member, when the inner and outer conductive features are approximately aligned.

4. The system of claim 3, wherein the conductive segment of the inner member of the tool comprises a conductive material within a wall of the inner member; and the conductive segment of the deployment tube of the tool comprises a conductive material within a wall of the deployment tube.

5. The tool of claim 3, wherein the conductive segment of the inner member of the tool comprises a conductive insert joined to a wall of the inner member; and the conductive segment of the deployment tube of the tool comprises a conductive insert joined to the wall of the deployment tube.

6. The system of claim 1, wherein:
the housing of the device further includes a snare attachment feature located between the proximal end of the device housing and the sensing extension;
the tool further includes a snare member including an elongate shaft extending within the lumen of the inner member, and a loop coupled to a distal end of the shaft, the distal end of the shaft being located in proximity to the distal end of the inner member; and the loop of the snare member is adapted to open and close around the snare attachment feature of the device via movement of the shaft of the snare member within the lumen of the inner member.

7. The system of claim 1, wherein the sense electrode of the device extension is spaced apart from the proximal end of the device housing by a distance of between approximately 6 cm and approximately 10 cm.

8. The system of claim 1, wherein the sense electrode of the device extension is spaced apart from the proximal end of the device housing by a distance of between approximately 10 cm and approximately 15 cm.

9. A method for deploying an implantable medical device, the device including an electronic controller, an hermetically sealed housing containing the controller, a fixation member coupled to a distal end of the housing, and a sensing extension coupled to the controller, the extension extending externally from a proximal end of the housing, the extension including a sense electrode, and the method comprising:

loading the device into a distal-most portion of a deployment tube of a delivery tool, such that the proximal end of the device housing abuts a distal end of an inner member of the tool, the inner member extending within a lumen formed by the deployment tube;

advancing the delivery tool, with the device loaded therein, into a venous system of a patient, such that the distal-most portion of the deployment tube is located in a right ventricle of the patient and abuts a target implant site;

retracting the deployment tube with respect to the inner member and the device to expose the fixation member of the device while pushing the inner member to engage the fixation member with tissue at the target implant site;

evaluating atrial sensing of the sense electrode of the device, after engaging the fixation member of the device, and while the sensing extension of the device remains contained within the lumen of the inner member and within the deployment tube; and withdrawing the tool from over an entirety of the device, if evaluating the atrial sensing confirms adequate atrial sensing.

10. The method of claim 9, further comprising:

advancing distally a shaft of a snare member of the tool relative to the inner member, to open a loop of the snare member, thereby releasing a snare attachment feature of the device from the loop, after evaluating the atrial sensing, and if evaluating the atrial sensing confirms adequate atrial sensing, and prior to withdrawing the tool from over an entirety of the device;

wherein the shaft of the snare member extends within the lumen of the inner member, the loop being coupled to a distal end of the shaft; and the snare attachment feature of the device is located between the proximal end of the device housing and the sensing extension.

\* \* \* \* \*